US009149557B2

(12) United States Patent
Kawamura et al.

(10) Patent No.: US 9,149,557 B2
(45) Date of Patent: Oct. 6, 2015

(54) PROCESS FOR PREPARING BIOABSORBABLE SHEET PREPARATION HOLDING THROMBIN

(75) Inventors: Ryoichi Kawamura, Kikuchi (JP); Takayuki Imamura, Kikuchi (JP); Hitomi Owaki, Kikuchi (JP)

(73) Assignee: THE CHEMO-SERO-THERAPEUTIC RESEARCH INSTITUTE, Kumamoto-shi (JP)

( * ) Notice: Subject to any disclaimer, the term of this patent is extended or adjusted under 35 U.S.C. 154(b) by 1023 days.

(21) Appl. No.: 12/988,241

(22) PCT Filed: Apr. 15, 2009

(86) PCT No.: PCT/JP2009/057584
§ 371 (c)(1),
(2), (4) Date: Oct. 15, 2010

(87) PCT Pub. No.: WO2009/128474
PCT Pub. Date: Oct. 22, 2009

(65) Prior Publication Data
US 2011/0038847 A1 Feb. 17, 2011

(30) Foreign Application Priority Data
Apr. 16, 2008 (JP) .................... 2008-106682

(51) Int. Cl.
| A61K 38/43 | (2006.01) |
| A61L 15/44 | (2006.01) |
| A61L 15/64 | (2006.01) |
| A61L 31/14 | (2006.01) |
| A61L 31/16 | (2006.01) |
| A61K 38/00 | (2006.01) |

(52) U.S. Cl.
CPC ............ *A61L 15/44* (2013.01); *A61L 15/64* (2013.01); *A61L 31/148* (2013.01); *A61L 31/16* (2013.01); *A61K 38/00* (2013.01); *A61L 2300/214* (2013.01); *A61L 2300/418* (2013.01); *A61L 2300/802* (2013.01); *A61L 2400/04* (2013.01)

(58) Field of Classification Search
CPC ............ A61F 2250/0067; A61F 2013/00221; A61F 13/00063; A61F 2013/00927; A61K 38/4833; C12Y 304/21005; C12N 2533/56
See application file for complete search history.

(56) References Cited

U.S. PATENT DOCUMENTS

| 4,265,233 A | 5/1981 | Sugitachi et al. |
| 4,453,939 A | 6/1984 | Zimmerman et al. |
| 4,696,812 A | 9/1987 | Silbering et al. |
| 4,965,203 A | 10/1990 | Silbering et al. |
| 5,023,082 A | 6/1991 | Friedman et al. |
| 5,849,322 A | 12/1998 | Ebert et al. |
| 8,435,779 B2 * | 5/2013 | Connolly et al. ............. 435/214 |
| 2002/0110585 A1 | 8/2002 | Godbey et al. |
| 2003/0012818 A1* | 1/2003 | Schense et al. ............... 424/486 |
| 2003/0068297 A1* | 4/2003 | Jain ............................ 424/85.1 |
| 2004/0049187 A1 | 3/2004 | Burnett et al. |
| 2006/0002918 A1 | 1/2006 | Jiang et al. |
| 2006/0134769 A1* | 6/2006 | Connolly et al. ............. 435/214 |
| 2006/0240084 A1 | 10/2006 | Serafica et al. |
| 2007/0224254 A1* | 9/2007 | Yu et al. ....................... 424/449 |
| 2008/0286347 A1 | 11/2008 | Uchida et al. |

FOREIGN PATENT DOCUMENTS

| EP | 0 059 265 A1 | 9/1982 |
| EP | 0 221 700 A2 | 5/1987 |
| EP | 0 221 700 A3 | 5/1987 |
| EP | 1 563 856 A1 | 8/2005 |
| JP | 56-39782 | 4/1981 |
| JP | 61-59737 | 12/1986 |
| JP | 62-106028 | 5/1987 |
| JP | 63-192723 | 8/1988 |
| JP | 1 501621 | 6/1989 |
| JP | 2-53732 | 2/1990 |
| JP | 5-163157 | 6/1993 |
| JP | 7-165604 | 6/1995 |
| JP | 7-64747 | 7/1995 |
| JP | 9-504719 | 5/1997 |
| JP | 11 513983 | 11/1999 |
| JP | 2000-510357 | 8/2000 |
| JP | 2001-513368 | 9/2001 |
| JP | 2002-515300 | 5/2002 |
| JP | 2002-193832 | 7/2002 |
| JP | 2003 515556 | 5/2003 |
| JP | 2004 512314 | 4/2004 |
| JP | 2005 532073 | 10/2005 |
| JP | 2006-117678 | 5/2006 |
| JP | 2006-306759 | 11/2006 |
| JP | 2007 246419 | 9/2007 |
| JP | 2007-246419 | 9/2007 |

(Continued)

OTHER PUBLICATIONS

International Search Report issued Jun. 16, 2009 in PCT/JP09/057584 filed Apr. 15, 2009.

Extended European Search Report issued on Apr. 5, 2013 in the corresponding European Application No. 09733482.5.

*Primary Examiner* — Blaine Lankford
(74) *Attorney, Agent, or Firm* — Oblon, McClelland, Maier & Neustadt, L.L.P.

(57) ABSTRACT

A process for preparing a bioabsorbable sheet preparation holding thrombin is provided. A process for preparing a bioabsorbable sheet preparation holding thrombin which comprises immersing a bioabsorbable sheet consisting of polyglycolic acid in a thrombin solution containing thrombin as an active ingredient, glycerol as a softening agent, Tween 80 as a permeating agent, and optionally histidine and trehalose as a stabilizing agent followed by drying to hold thrombin on said bioabsorbable sheet, and a bioabsorbable sheet preparation holding thrombin prepared by said process.

13 Claims, 11 Drawing Sheets

(56) References Cited

FOREIGN PATENT DOCUMENTS

| | | |
|---|---|---|
| JP | 2008 503240 | 2/2008 |
| WO | WO 95/12371 | 5/1995 |
| WO | WO 97/15297 | 5/1997 |
| WO | WO 97/37694 | 10/1997 |
| WO | WO 99/07417 | 2/1999 |
| WO | WO 99/59647 | 11/1999 |
| WO | WO 01/39756 A1 | 6/2001 |
| WO | WO 2004/007707 A1 | 1/2004 |
| WO | WO 2004/043503 A1 | 5/2004 |
| WO | WO 2006/009989 A1 | 1/2006 |
| WO | 2006 033433 | 3/2006 |
| WO | 2006 113796 | 10/2006 |

\* cited by examiner

PROCESS FOR PREPARING BIOABSORBABLE SHEET PREPARATION HOLDING THROMBIN

TECHNICAL FIELD

The present invention relates to a process for preparing a bioabsorbable sheet preparation holding thrombin. Specifically, the present invention relates to a process for preparing a bioabsorbable sheet preparation holding thrombin which comprises immersing a bioabsorbable support in a sheet form in a solution containing thrombin as an active ingredient, a polyhydric alcohol, a detergent, an amino acid and an oligosaccharide as an additive followed by drying and a bioabsorbable sheet preparation holding thrombin prepared by the process.

BACKGROUND OF THE INVENTION

Thrombin is an enzyme that is involved in blood coagulation and is indispensable to maintenance and progress of life such as formation of hemostatic thrombus or treatment of injury. Thrombin is normally present in blood in the form of inactive prothrombin but is activated by the coagulation system triggered by, for instance, platelets or damage in tissue cells to convert fibrinogen in a soluble form into insoluble fibrin useful for hemostasis and treatment of injury. A hemostatic utilizing this principle has widely been applied in clinical scenes.

Although thrombin has been used as an active ingredient of a hemostatic, with the conventional hemostatic in the form of liquid, hemostasis by pressing or closing by pressing to a spot of gushing hemorrhage or oozing hemorrhage is not possible and therefore bleeding cannot be stopped.

Aiming at hemostasis of such gushing hemorrhage or oozing hemorrhage, there have been attempts to develop a sheet-type hemostatic where thrombin, fibrinogen and/or a coagulation factor is held on a collagen sponge, a non-woven fabric consisting of alginic acid or polyglycolic acid, or other bioabsorbable supports consisting of gelatin or hydrogel (e.g. see Patent references 1, 2, 3, 4, 5, 6 and 7).

However, most of the sheet hemostatic have not yet been put into practical usage due to problems that they are thick and lack flexibility since, when applied to a closing spot of organs in their dry form, rigidity of supports per se may adversely affect to thereby make it difficult to closely contact with a spot of injury, thus failing to exert sufficient adhesive effect.

A unique product of a sheet-type fibrin adhesive that has been commercially available is one where fibrinogen and bovine thrombin are held on a support consisting of equine collagen (product name: TachoComb/CSL Behling) (e.g. see Patent reference 8). However, this adhesive still has room for improvement in handling and removal of risk factors in view of its thickness (about 3 mm) and inclusion of components derived from animals.

On the other hand, there are several reports on a stabilizing agent to thrombin. For instance, approaches for preserving thrombin with stability has been reported by comprising a salt of an organic carboxylic acid (e.g. see Patent reference 9) or glycerol (e.g. see Patent references 10, 11 and 12) for a liquid preparation, or by comprising a sugar, a basic amino acid and a liquid organic acid (e.g. see Patent reference 13), or gelatin, glycine and a sugar (e.g. see Patent reference 14), or an aliphatic polybasic carboxylic acid and albumin (e.g. see Patent reference 15), or human serum albumin and an amino acid (e.g. see Patent reference 16) for a dry preparation packed in a vial or in an aluminum pouch package. However, in case of a sheet-type preparation, mere stabilization of thrombin cannot attain an object.

When a sheet preparation is used, it is sometimes made round or folded so that it may touch closely a spot of injury. Therefore, for avoiding breakage of a sheet or leakage of thrombin constituent due to forces imposed, it is necessary to improve flexibility or thrombin-holding property of a sheet.

For instance, the thrombin preparation comprising a sugar, a basic amino acid and a liquid organic acid as described above is not suited for a sheet-type preparation since flexibility is lost when the thrombin preparation is held on a sheet. Also, when a non-woven fabric is immersed in a thrombin solution and is simply subject to lyophilization, thrombin is not held on the non-woven fabric. In order to solve the problems, a technique is reported that a non-woven fabric made of chitin as a support is immersed alternately in three solutions, i.e. a solution of an acidic high molecular weight compound such as chondroitin sulfate, alginic acid or hyaluronic acid, a solution of a basic high molecular weight compound such as chitosan, and a thrombin solution, to hold thrombin, followed by drying in vacuum or with ventilation to prepare a sheet-like hemostatic or a sheet-like medicament for injury (e.g. see Patent reference 17). However, with such technique of alternate absorption, even if flexibility of a sheet could be secured, reduction of the activity of thrombin would be unavoidable and handling in production is cumbersome. Accordingly, development of a more efficient process for preparation is desired.

Patent reference 1: Japanese Patent Publication No. 61-59737
Patent reference 2: Japanese Patent Publication No. 05-163157
Patent reference 3: Japanese Patent Publication No. 2002-515300
Patent reference 4: U.S. Pat. No. 4,453,939
Patent reference 5: Japanese Patent Publication No. 9-504719
Patent reference 6: Japanese Patent Publication No. 2000-510357
Patent reference 7: Japanese Patent Publication No. 2001-513368
Patent reference 8: European Patent 0059265
Patent reference 9: Japanese Patent Publication No. 56-39782
Patent reference 10: Japanese Patent Publication No. 62-106028
Patent reference 11: Japanese Patent Publication No. 7-64747
Patent reference 12: Japanese Patent Publication No. 63-192723
Patent reference 13: Japanese Patent Publication No. 2-53732
Patent reference 14: Japanese Patent Publication No. 7-165604
Patent reference 15: Japanese Patent Publication No. 2002-193832
Patent reference 16: Japanese Patent Publication No. 2006-117678
Patent reference 17: Japanese Patent Publication No. 2006-306759

DISCLOSURE OF THE INVENTION

Technical Problem to be Solved by the Invention

As described above, although a sheet-type preparation comprising thrombin as an active ingredient has already been developed, there still remains room for improvement in view of flexibility of a sheet preparation, stability and holding of thrombin, as well as cumbersome process for preparation and exclusion of unknown risk factors.

Accordingly, an object of the present invention is to provide an expedient process for preparing a bioabsorbable sheet preparation holding thrombin and a bioabsorbable sheet preparation holding thrombin obtained by said process.

Means for Solving the Problems

In order to attain the object as described above, the present inventors have assiduously investigated, and as a result, have found that an excess production of lyophilized powder could be inhibited, and flexibility of a sheet preparation could be maintained, by comprising glycerol in a thrombin solution, and as a consequence, that the loss or destruction of thrombin constituent on a non-woven fabric due to fugacity of powder after drying could be avoided. Further, the present inventors have found that addition of Tween 80 enhanced permeation of thrombin into a non-woven fabric and that addition of trehalose and a small amount of histidine markedly increased stability of thrombin as compared to separate addition of trehalose or histidine, each alone, when a dry preparation is produced. As such, the present inventors have completed the present invention. Thus, the present invention is as described below.

[1] A process for preparing a bioabsorbable sheet preparation which comprises the following steps (1) to (3):
 (1) Step of mixing an active ingredient with a solution comprising a softening agent and a permeating agent;
 (2) Step of adding dropwise the solution of (1) to a bioabsorbable sheet or immersing a bioabsorbable sheet in the solution of (1); and
 (3) Step of drying the bioabsorbable sheet of (2).
[2] The process of [1] above wherein the active ingredient is thrombin or fibrinogen.
[3] The process of [2] above wherein thrombin is at a concentration of 1,000 to 2,000 Units/mL.
[4] The process of any of [1] to [3] above wherein the softening agent is a polyhydric alcohol or glycosaminoglycan and the permeating agent is a detergent.
[5] The process of [4] above wherein the polyhydric alcohol is selected from the group consisting of glycerol, propylene glycol, butylene glycol and Sorbit, the glycosaminoglycan is selected from the group consisting of hyaluronic acid, chondroitin sulfate, keratan sulfate and heparan sulfate, and the detergent is selected from the group consisting of Tween 80, poly(oxyethylene) lauryl ether (Brij 35), Pluronic F-68, Sucrose monolaurate, Sodium Cholate, Tween 20, Triton X-100, Nonidet P40, sulfuric-3-[(3-cholamidpropyl)dimethylammonio]-1-propane (CHAPS), n-Octylglucoside), n-Dodecylmaltoside and Digitonin.
[6] The process of any of [1] to [5] above wherein the solution further comprises an amino acid and an oligosaccharide.
[7] The process of [6] above wherein the amino acid is selected from the group consisting of arginine, histidine, lysine, glutamic acid, glycine and aspartic acid and the oligosaccharide is selected from the group consisting of mannitol, sucrose, trehalose, sorbitol and erythritol.
[8] The process of any of [1] to [3] above wherein the solution comprises glycerol, Tween 80, histidine and trehalose as an additive.
[9] The process of any of [1] to [8] above wherein the softening agent is at a concentration of 1 to 2% and the permeating agent is at a concentration of 0.01 to 1%.
[10] The process of any of [6] to [9] above wherein the amino acid is at a concentration of 2.4 to 180 mM and the oligosaccharide is at a concentration of 5 to 40 mg/mL.
[11] The process of any of [1] to [10] above wherein the bioabsorbable sheet is synthesized from a substrate selected from the group consisting of polyglycolic acid, polylactic acid, carboxymethyl cellulose, chitin, chitosan, alginic acid, collagen, gelatin and hydrogel.
[12] A bioabsorbable sheet preparation holding thrombin which comprises thrombin as an active ingredient, and a softening agent, a permeating agent, an amino acid and a small amount of an oligosaccharide as an additive.
[13] The preparation of [12] above wherein thrombin is at a concentration of 1,000 to 2,000 Units/mL.
[14] The preparation of [12] or [13] above wherein the softening agent is a polyhydric alcohol or glycosaminoglycan and the permeating agent is a detergent.
[15] The preparation of [14] above wherein the polyhydric alcohol is selected from the group consisting of glycerol, propylene glycol, butylene glycol and Sorbit, the glycosaminoglycan is selected from the group consisting of hyaluronic acid, chondroitin sulfate, keratan sulfate and heparan sulfate, and the detergent is selected from the group consisting of Tween 80, poly(oxyethylene) lauryl ether (Brij 35), Pluronic F-68, Sucrose monolaurate, Sodium Cholate, Tween 20, Triton X-100, Nonidet P40, sulfuric-3-[(3-cholamidpropyl)dimethylammonio]-1-propane (CHAPS), n-Octylglucoside), n-Dodecylmaltoside and Digitonin.
[16] The preparation of any of [12] to [15] above wherein the amino acid is selected from the group consisting of arginine, histidine, lysine, glutamic acid, glycine and aspartic acid and the oligosaccharide is selected from the group consisting of mannitol, sucrose, trehalose, sorbitol and erythritol.
[17] The preparation of [12] or [13] above wherein the preparation comprises glycerol, Tween 80, histidine and trehalose as an additive.
[18] The preparation of any of [12] to [17] above wherein the softening agent is at a concentration of 1 to 2%, the permeating agent is at a concentration of 0.01 to 1%, the amino acid is at a concentration of 2.4 to 180 mM and the oligosaccharide is at a concentration of 5 to 40 mg/mL.
[19] The preparation of any of [12] to [18] above wherein the bioabsorbable sheet is synthesized from a substrate selected from the group consisting of polyglycolic acid, polylactic acid, carboxymethyl cellulose, chitin, chitosan, alginic acid, collagen, gelatin and hydrogel.

Use of a polyhydric alcohol as a softening agent for a bioabsorbable sheet preparation.
[21] Use of [20] above wherein the polyhydric alcohol is selected from the group consisting of glycerol, propylene glycol, butylene glycol and Sorbit.
[22] Use of [20] or [21] above wherein the polyhydric alcohol is at a concentration of 1 to 2%.
[23] Use of any of [20] to [22] above wherein the bioabsorbable sheet is synthesized from a substrate selected from the group consisting of polyglycolic acid, polylactic acid, carboxymethyl cellulose, chitin, chitosan, alginic acid, collagen, gelatin and hydrogel.
[24] Use of any of [20] to [23] above wherein the bioabsorbable sheet preparation is such that thrombin or fibrinogen is held on the bioabsorbable sheet.
[25] Use of a detergent as a permeating agent for an active ingredient in a bioabsorbable sheet preparation.
[26] Use of [25] above wherein the detergent is selected from the group consisting of Tween 80, poly(oxyethylene) lauryl ether (Brij 35), Pluronic F-68, Sucrose monolaurate, Sodium Cholate, Tween 20, Triton X-100, Nonidet P40, sulfuric-3-[(3-cholamidpropyl)dimethylammonio]-1-propane (CHAPS), n-Octylglucoside), n-Dodecylmaltoside and Digitonin.
[27] Use of [25] or [26] above wherein the detergent is at a concentration of 0.01 to 1%.

[28] Use of any of [25] to [27] above wherein the bioabsorbable sheet is synthesized from a substrate selected from the group consisting of polyglycolic acid, polylactic acid, carboxymethyl cellulose, chitin, chitosan, alginic acid, collagen, gelatin and hydrogel.

[29] Use of any of [25] to [28] above wherein the bioabsorbable sheet preparation is such that thrombin or fibrinogen is held on the bioabsorbable sheet.

Effects of the Invention

In accordance with the present invention, a bioabsorbable sheet preparation holding thrombin and a process for preparing the same are provided. The bioabsorbable sheet preparation holding thrombin of the present invention may be prepared, for instance, by immersing a bioabsorbable sheet consisting of polyglycolic acid in a thrombin solution comprising glycerol, Tween 80, trehalose and a small amount of histidine, followed by lyophilization. By comprising glycerol, dropping off of thrombin constituent from a bioabsorbable sheet may be avoided and a bioabsorbable sheet preparation holding thrombin is endowed with flexibility. By comprising Tween 80, permeation of thrombin into a bioabsorbable sheet may be enhanced to facilitate holding of thrombin. Further, by comprising trehalose and a small amount of histidine, the activity of thrombin may sufficiently be maintained when a dry preparation is produced. Accordingly, the present invention may facilitate production of a bioabsorbable sheet preparation holding thrombin. A bioabsorbable sheet preparation holding thrombin as prepared by the process of the present invention may possess stability of thrombin and flexibility necessary for a bioabsorbable sheet preparation.

Also, with the bioabsorbable sheet preparation holding thrombin of the present invention, since thrombin may be eluted into a solution quite rapidly, thrombin may exert its enzymatic activity immediately after a sheet holding thrombin is in contact with liquid fibrinogen or blood. Namely, it is expected that, with the bioabsorbable sheet preparation holding thrombin of the present invention, thrombin may be eluted rapidly at the surface to be closed by adhesion or at active bleeding spot to exert its enzymatic activity with fibrinogen as a substrate to promptly provide fibrin conversion, providing tissue adhesion/closing effect and hemostatic effect.

BEST MODE FOR CARRYING OUT THE INVENTION

Figure 1:
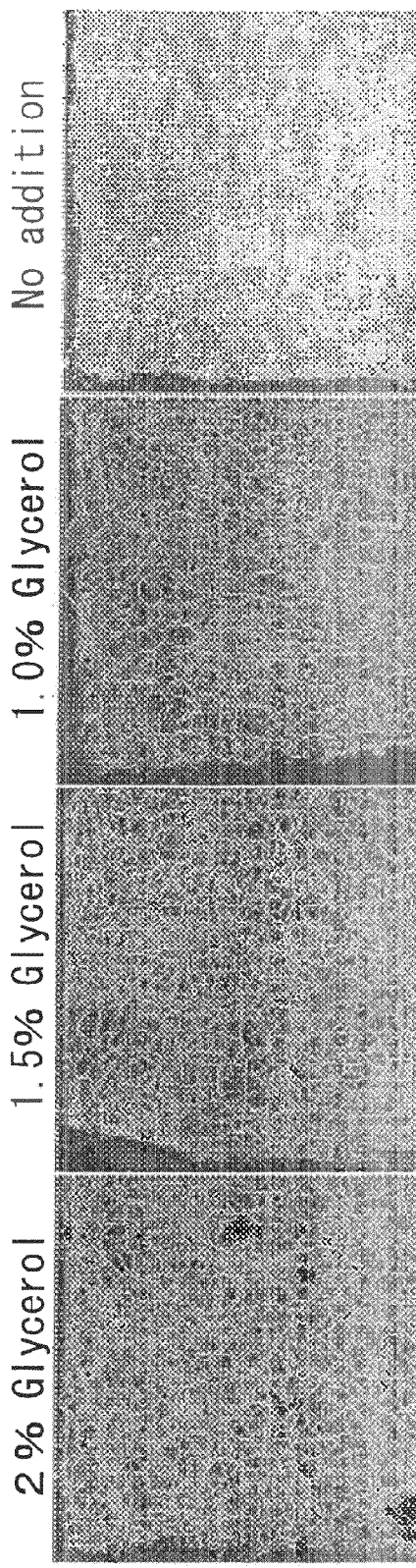
FIG. 1 shows configurations of a bioabsorbable sheet preparation holding thrombin prepared with a thrombin solution with and without addition of glycerol.

The present invention is characterized by a process for preparing a bioabsorbable sheet preparation holding thrombin, which process utilizes a solution comprising a polyhydric alcohol, which is effective as a softening agent for the preparation, a detergent, which serves as enhancing permeation of thrombin into a bioabsorbable sheet, and a specific amino acid and an oligosaccharide, which maintains stability of thrombin, and a bioabsorbable sheet preparation holding thrombin obtained by said process.

A thrombin constituent as used herein may be either thrombin commercially available (e.g. Thrombin from human Plasma (Sigma-Aldrich, code No. T6884 etc.)), or thrombin from the living body as prepared from animal blood by a low-temperature ethanol fractionation or chromatography, or a recombinant thrombin obtained by a recombinant DNA technique. Preferably, a recombinant thrombin may be used so as to exclude contamination with unknown infectious factors or risk factors. In case that a recombinant DNA technique is used, a thrombin gene may preferably be taken from an animal species to which hemostasis is to be applied.

In the living body, thrombin is synthesized as a precursor prothrombin in a vitamin K-dependent manner in hepatocytes and is subject to limited degradation by FXa-FVa on phospholipids of the cellular membrane (cleavage occurs at two sites, Arg320-ILe321 and Arg271-Thr272, of prothrombin) to generate thrombin. In case that thrombin is obtained by a recombinant DNA technique, expression may firstly be done for prothrombin which is, after purification, treated with ecarin to convert into thrombin.

For instance, a human prothrombin gene may be prepared starting from a whole RNA, mRNA or a genomic DNA in accordance with a general recombinant DNA technique as taught by Sambrook et al., Molecular Cloning, A Laboratory Manual Second Edition. Cold Spring Harbor Laboratory Press, N.Y., 1989. Today, various kits are commercially available and may be used. For instance, reagents such as TRIzol reagent (Invitrogen), ISOGEN (NIPPON GENE CO., LTD.), StrataPrep Total RNA Purification Kit (TOYOBO) for extraction of RNA; kits such as mRNA Purification Kit (Amersham Bioscience), Poly(A) Quick mRNA Isolation Kit (TOYOBO), mRNA Separator Kit (Clontech) for purification of mRNA; T-Primed First Strand Kit (Amersham Pharmacia), SuperScript plasmid system for cDNA synthesis and plasmid cloning (Invitrogen), cDNA Synthesis Kit (TAKARA SHUZO CO., LTD.), SMART PCR cDNA Synthesis & Library Construction Kits (Clontech), Directionary cDNA Library Construction systems (Novagen Inc.), GeneAmp PCR Gold (Applied Biosystems) for conversion into cDNA may be used.

The thus obtained human thrombin gene may be inserted into a suitable expression vector and transformation of a host cell, e.g. an animal cell, with the resultant expression vector may be conducted. An expression vector as used herein is not particularly limited but may be added with an expression regulator region such as a promoter suitable for an exogenous gene, termination codon, poly A addition signal sequence, kozack sequence, secretion signal, and the like. A promoter contained in said expression vector may be any insofar as it leads to expression of an exogenous gene, such as an SV40 early promoter, an SV40 late promoter, a Cytomegalovirus promoter, a chicken β-actin promoter, as selected based on an animal cell to be used as a host. Preferably, a chicken β-actin promoter-based expression plasmid pCAGG (Japanese patent publication No. 3-168087) may be used. A marker gene for selection or gene amplification may be one commonly known in the art such as a neo gene, a dihydrofolate reductase (dhfr) gene, a puromycin resistant enzyme gene, or a glutamine synthetase (GS) gene.

A host as used herein may be any culture cell from various mammals and includes Chinese hamster ovary cell (CHO cell), 293 cell derived from human, cells derived from chicken, and the like. Gene introduction into an animal cell may be performed, with no specific limitation, by e.g. a phosphate calcium method, a DEAE dextran method, a method using lipofectin liposome, a protoplast polyethylene glycol fusion, electroporation etc., which may suitably be selected depending on a host cell as used (Molecular Cloning (3rd Ed.), Vol. 3, Cold Spring Harbor Laboratory Press (2001)). A medium to be used in culture includes an agar medium, a liquid medium, as classified from its form, or YMM-01, DMEM, RPMI, αMEM, etc. and may suitably be selected depending on a cell, the purpose of culture or a stage of culture. In accordance with respective protocols, a culture medium may be used in which sera, amino acids, vitamins, sugars, antibiotics, pH adjusting buffers, and the like are added. pH of media may be adjusted in a range of 6-8 and a culture temperature may be in a range of 30° C. to 39° C. An amount of a medium, any additive and a culture period may suitably be adjusted depending on a culture scale.

Cells producing a human prothrombin may be obtained by detecting a human prothrombin present in a culture solution of the cloned drug-resistant cells by a detection method utilizing a specific reaction with an anti-thrombin antibody such as dot blot, Western blot, sandwich ELISA, etc. The thus obtained cells producing a human prothrombin may be adapted to a serum-free culture medium and then subject to culture in a large amount at a level of industrial production. Culture in a large amount may be done by e.g. fed batch culture, batch culture, etc. with no specific limitation.

For purification of a human prothrombin from the cells producing a human prothrombin, a purification method as generally used in protein chemistry may be used such as e.g. a salting out, a ultrafiltration, an isoelectric precipitation, an electrophoresis, an ion exchange chromatography, a gel filtration chromatography, an affinity chromatography, an hydrophobic chromatography, a hydroxyapatite chromatography, etc. In practice, a combination of the above methods may sometimes be employed due to presence of a variety of cellular debris.

A recombinant ecarin may preferably be used for conversion of human prothrombin into human thrombin. A recombinant ecarin may be prepared as described in the patent publication (WO2003/004641). Briefly, a snake venom ecarin cDNA is prepared as taught by Nishida et al. (S, Nishida et al., Biochemistry, 34, 1771-1778, 1995) and incorporated into a chicken β-actin promoter-based expression plasmid pCAGG as used herein. The obtained expression vector is introduced into animal cells, e.g. CHO cells, to provide cells producing a recombinant ecarin. A recombinant ecarin may be purified by a cation exchange chromatography and a gel filtration. The thus purified recombinant ecarin may be acted to a human prothrombin for conversion into human thrombin. The reaction condition may be the same as that of a normal enzymatic reaction. For instance, ecarin at a final concentration of 2-8 Units/mL may be added to a human prothrombin at 1000 μg/mL for reaction at 36-38° C. for 1-4 hours to complete conversion of a human prothrombin into a human thrombin.

In case that human thrombin is purified from the solution after treatment with ecarin, it may be done by subjecting the solution to the method for purifying a protein as described above. Preferably, a method for purification using a combination of a benzamidine chromatography and a cation exchange chromatography may be used. For a benzamidine chromatography, human thrombin may be adsorbed to a column equilibrated with a buffer containing 0.3-0.7 M NaCl, pH 7-9, and after washing with the buffer, may be eluted with the buffer supplemented with 0.1 M benzamidine hydrochloride.

Next, the above eluate of human thrombin may be subject to a cation exchange chromatography. A cation exchanger such as a sulfopropyl type or a carboxymethyl type has been developed and may be selected as appropriate for use. SP Toyopearl 550C (Tosoh Corporation) is used in the present invention. Human thrombin may be adsorbed to a column equilibrated with 10 mM citrate buffer containing 0.2 M NaCl, pH 6-7, and after washing with the buffer, may be eluted with the buffer containing 0.6 M NaCl. By these procedures, a human thrombin of high purity may be obtained.

Unit of activity of the thus obtained human thrombin may be indicated by clotting activity and the activity to cleave a synthetic substrate (S-2238). A value for the clotting activity represents a time required for clotting by fibrinogen relative to a calibration curve of standard, including thrombin of the Japanese Pharmacopoeia standard and WHO international standard (NIBSC). The activity to cleave S-2238, which is based on a reaction between thrombin and its specific substrate, may be measured by determining an amount of p-nitroaniline released upon cleavage of the synthetic substrate S-2238 by thrombin through a change in absorbance at OD405/650.

The thus obtained recombinant human thrombin (hereinafter also referred to as merely "thrombin") may be held on a bioabsorbable sheet. A bioabsorbable sheet may be in any form insofar as flexibility and elasticity are ensured to some extent such as a textile, woven fabric or non-woven fabric prepared by processing a bioabsorbable synthetic fiber into sheet. A bioabsorbable synthetic fiber may be selected from the group consisting of polyglycolic acid, polylactic acid, carboxymethyl cellulose, chitin, chitosan, alginic acid, collagen, gelatin and hydrogel. Preferably, polyglycolic acid non-woven fabric may be used which is prepared by knitting or weaving polyglycolic acid as a substrate and needle-punching the knit or fabric to prepare a non-woven fabric.

To a solution used for holding thrombin on a bioabsorbable sheet (hereinafter also referred to as "thrombin solution") may be added not only thrombin as an active ingredient of a hemostatic but also a stabilizing agent for maintaining the activity of thrombin per se, a softening agent for avoiding the loss or fugacity of thrombin constituent held on a bioabsorbable sheet, and a permeating agent for enhancing permeation of thrombin into a bioabsorbable sheet. Thrombin may be contained in a thrombin solution at such a concentration that the hemostatic activity is exerted, e.g. at a final concentration of 100 to 5,000 Units/mL, preferably at 1,000 to 2,000 Units/mL.

The loss or decrease in the activity of thrombin is due to aggregation of thrombin while storage. Thus, for a stabilizing agent of thrombin, a substance capable of inhibiting aggregate formation of thrombin may be used. Such a substance may include a protein, e.g. albumin, a specific amino acid, and an oligosaccharide.

An amino acid may include arginine, histidine, lysine, glutamic acid, glycine and aspartic acid. Glutamic acid and histidine are expected to be particularly effective as a stabilizing agent. For glutamic acid, however, when used in a large amount, there is a danger of neurotoxicity. Therefore, in view of safety, histidine may preferably be used. A final concentration of an amino acid may be in a range of 2.4 to 180 mM.

An oligosaccharide may be used that effectively maintains the activity of thrombin while storage. Such an oligosaccharide may include mannitol, sucrose, trehalose, sorbitol and erythritol. It is reported that trehalose, if supplied to the organ surface at surgical operation, may inhibit denaturation of the tissue and to prevent dry adhesion (http://www.vm.a.u-tokyo.ac.jp/vmc/achievement/treharose.html, or http://www.next21.info/press/images/20050624Treha.pdf). Therefore, trehalose is expected to be effective not only as a stabilizing agent but also for decreasing adhesion of the surface to be treated for closure with other organs. Thus, trehalose may preferably be used. A final concentration of an oligosaccharide may be in a range of 5 to 40 mg/mL.

By using an amino acid and an oligosaccharide together, a synergetic effect in stabilizing thrombin may be obtained as compared to the effect exerted when they are used each alone. Therefore, a thrombin solution of the present invention may contain both an amino acid and an oligosaccharide and a ratio of these two may suitably be adjusted within the ranges as described above. Preferably, an amino acid at 22.5 to 180 mM and an oligosaccharide at 30 to 40 mg/mL may be used. The most preferable embodiment is histidine at 180 mM and trehalose at 40 mg/mL.

A softening agent and a permeating agent may be used that may not affect the activity of thrombin and that may maintain flexibility of a bioabsorbable sheet. Such a softening agent may include a polyhydric alcohol and glycosaminoglycan such as hyaluronic acid, chondroitin sulfate, keratan sulfate and heparan sulfate, preferably a polyhydric alcohol. A polyhydric alcohol may include glycerol, propylene glycol, butylene glycol and Sorbit. Glycerol may preferably be used since it has efficaciously been used as a stabilizing agent in various medicaments and vaccines. A softening agent may be used at a final concentration in a range of 1 to 2%.

For a permeating agent, a detergent may be used such as Tween 80, poly(oxyethylene) lauryl ether (Brij 35), Pluronic F-68, Sucrose monolaurate, Sodium Cholate, Tween 20, Triton X-100, Nonidet P40, sulfuric-3-[(3-cholamidpropyl)dimethylammonio]-1-propane (CHAPS), n-Octylglucoside, n-Dodecylmaltoside and Digitonin, preferably Tween 80. A permeating agent may be used at a concentration in a range of 0.01 to 1%, preferably 0.01 to 0.1%. A softening agent and a permeating agent of the present invention may be used not only in a bioabsorbable sheet preparation holding thrombin but also in a bioabsorbable sheet preparation holding other hemostatic proteins, e.g. fibrinogen.

A buffer used for preparing a thrombin solution may include a phosphate buffer, Tris buffer, a citrate buffer, and the like, at a pH range of 6.0 to 8.0. Other additives such as a salt, e.g. calcium chloride, sodium chloride, or excipients such as sucrose and mannitol in an appropriate amount may be added as appropriate.

A bioabsorbable sheet preparation holding thrombin of the present invention may be obtained, for instance, by adding dropwise a thrombin solution to a bioabsorbable sheet consisting of polyglycolic acid put in an appropriate container or immersing the bioabsorbable sheet in a thrombin solution in a container and, after lyophilization at −80° C., drying the sheet. Alternatively, a bioabsorbable sheet filled with a thrombin solution may be subject to natural drying. By comprising a permeating agent in a thrombin solution, permeability of thrombin into the bioabsorbable sheet may be enhanced. During the while moisture is removed by drying, thrombin may stably be held on the fibers of the bioabsorbable sheet wrapped in a stabilizing agent and a softening agent. The obtained bioabsorbable sheet preparation holding thrombin may be stored at room temperature (22 to 25° C.) with tight sealing and packaging in a two-layered (polyethylene-aluminum) film pack together with a drying agent.

Estimation of the thus obtained bioabsorbable sheet preparation holding thrombin may be carried out by testing a holding rate of thrombin held on a bioabsorbable sheet, flexibility of a bioabsorbable sheet preparation holding thrombin after molding, stability of thrombin, and the like.

A holding rate of thrombin on a bioabsorbable sheet may be calculated by comparing the activity of thrombin eluted from the sheet after immersing the sheet in a saline or a suitable buffer and shaking with the activity of thrombin held on the sheet. For the measurement of the activity of thrombin, the clotting activity and the activity to cleave a synthetic substrate as described above may be used. In accordance with the present invention, a bioabsorbable sheet preparation holding thrombin with a holding rate of 80% or more may be obtained.

Flexibility of a bioabsorbable sheet preparation holding thrombin of the present invention may be estimated as described below. Namely, a bioabsorbable sheet holding thrombin is cut into an appropriate piece and one end of the piece is fixed on a pedestal. A fibrinogen solution prepared at about 55 mg/mL is then added dropwise to the portion horizontally projecting from the pedestal. The fibrinogen is immediately converted into fibrin by the action of thrombin held on the bioabsorbable sheet to let the sheet be hanged downward by the weight of fibrin. Flexibility may be estimated by measuring how much the tip of the projecting portion is hanged down from the horizontal level line.

Stability of a bioabsorbable sheet preparation holding thrombin of the present invention may be estimated by evaluating the remnant enzymatic activity of thrombin and an extent of aggregation or degradation of a thrombin molecule after storage for a long period of time. The remnant enzymatic activity of thrombin may be tested by measuring the enzymatic activity in the same manner as in the test of a holding rate of thrombin as described above. An extent of aggregation or degradation of a thrombin molecule may be tested by subjecting a portion of thrombin eluted from the sheet to SDS-PAGE or size exclusion high performance liquid chromatography.

A bioabsorbable sheet preparation holding thrombin of the present invention may be used as an adhesive by applying the preparation to a spot of injury or hemostasis. Depending on severity of bleeding, the bioabsorbable sheet preparation holding thrombin may be applied either alone or together with fibrinogen, a constituent of a fibrin adhesive preparation.

For oozing hemorrhage that occurs at damage such as partial section or partial breakage of the liver or the spleen in the field of surgery of the digestive organs, a bioabsorbable sheet preparation holding thrombin may be applied alone to the affected surface followed by pressing for 3 to 5 minutes to accomplish hemostasis. On the other hand, if fibrinogen, a constituent of a fibrin adhesive preparation, is applied together, the closing effect or the hemostatic effect may be enhanced. For instance, in the filed of surgery of the respiratory organs, air leakage site may effectively be closed at a peeled surface of the lung pleura where expansion and contraction pressures of the lung are generated, a cut surface of the parenchyma of the lung lobe, or a cut edge of the bronchia. In case of oozing hemorrhage at around the uterus and the placenta where a network of numerous blood vessels are spread and there is a high risk of bleeding upon incision and excision, hemostatic treatment becomes extremely difficult due to indefiniteness of bleeding points but the present invention makes it possible to close a fixed area at a time with a single treatment.

It is for application to gushing hemorrhage at a damaged site of the artery where a high blood pressure is imposed or at treatment of suture of an artificial vessel that the present invention may exert the utmost effect, while maintaining a sufficient amount of fibrinogen at to affected site, to allow for formation of fibrin promptly and rigidly to thereby accomplish hemostasis.

The adhesive and closing effect as described above is owing to the fact that a bioabsorbable sheet preparation holding thrombin of the present invention is highly flexible and hence may follow the unevenness of the tissue so as to be tightly adhered to and that thrombin is promptly eluted to convert fibrinogen into fibrin.

The present invention is explained in more detail by means of the following Examples but should not be construed to be limited thereto.

EXAMPLE

Example 1

Inhibition of Excess Formation of Lyophilized Dry Powder by Addition of Glycerol A thrombin solution (pH 6.0) containing glycerol at a final concentration of 1% or 1.5% or 2%, 1875 Units/mL thrombin, 10 mg/mL human serum albumin, 40 mM calcium chloride, 5 mg/mL mannitol and 0.1% Tween 80 was poured into a container, laid with a bioabsorbable sheet (a polyglycolic acid bioabsorbable synthetic non-woven fabric, Product name: Neoveil (Gunze Limited)), at 1 mm of thickness and, after lyophilization at −80° C. for 2 hours, dried in vacuum to prepare a bioabsorbable sheet preparation holding thrombin. This preparation was compared with a bioabsorbable sheet preparation holding thrombin prepared in the same manner as described above but with a thrombin solution not containing glycerol.

As shown in FIG. 1, excess formation of lyophilized dry powder, by addition of glycerol, was inhibited in a bioabsorbable sheet preparation holding thrombin.

Example 2

Effect of Addition of Glycerol on Stability of Thrombin

The bioabsorbable sheet preparations holding thrombin with and without addition of glycerol obtained in Example 1, as in a container, were put in a two-layered (polyethylene-aluminum) film pack together with a drying agent with tight sealing and packaging and stored at room temperature (22 to 25° C.). One, two, three and eight weeks after storage, the sample packages were opened, the bioabsorbable sheet preparations holding thrombin were peeled off from the containers and cut into pieces of 2 cm×2 cm (4 cm$^2$) which were immersed in a saline (1.0 mL) with thorough mixture to let thrombin be eluted. The resultant thrombin eluate was tested for the clotting activity in accordance with "Method for quantification of thrombin" of Japanese Pharmacopoeia. In the following, "Method for quantification of thrombin" is briefly explained.

Figure 2:
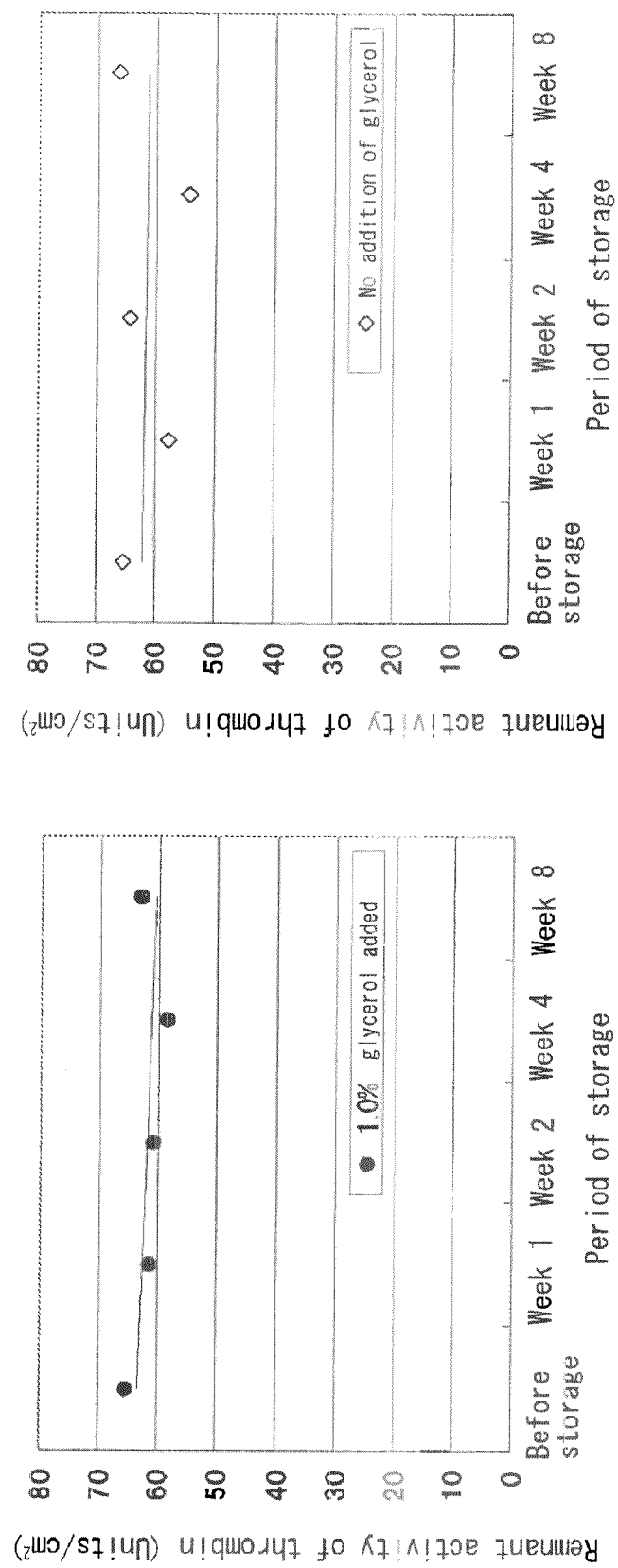
FIG. 2 shows a remnant activity of thrombin after storage for a fixed time in a bioabsorbable sheet preparation holding thrombin prepared with a thrombin solution with and without addition of glycerol.

First, a clotting time was defined as a time required, after mixing a fibrinogen solution and a thrombin solution, for attaining 0.3 of absorbance (450 nm) of the resulting solution containing fibrin. A standard solution (four kinds of units) prepared with thrombin standard of applicant's own was mixed with a fibrinogen solution at a fixed concentration and a clotting time was measured. A standard line showing a relationship between unit activity of thrombin and a clotting time was prepared where the axis of abscissas indicates the unit of activity and the axis of ordinates indicates the clotting time. A clotting time was measured in like manner for the above thrombin eluate and, using the standard line, unit of activity of thrombin was obtained and unit of remnant activity of thrombin per area of the sheet (Unit/cm$^2$) was calculated. FIG. 2 shows the remnant activity of thrombin in samples with and without addition of glycerol where the axis of abscissas indicates a period of time for storage and the axis of ordinates indicates unit of clotting activity (Unit/cm$^2$) of the thrombin eluate after storage as compared that before storage.

As a result of comparison between the samples with and without addition of glycerol, it was proved that addition of glycerol did not decrease the thrombin activity.

Example 3

Effect of Addition of Human Serum Albumin on Stability of Thrombin

Using the thrombin solution with addition of 1% glycerol obtained in Example 1 and two thrombin solutions which were the thrombin solution but devoid of albumin, bioabsorbable sheet preparations holding thrombin were prepared with tight sealing and packaging and stored at 37° C. as described in Examples 1 and 2.

Figure 3:
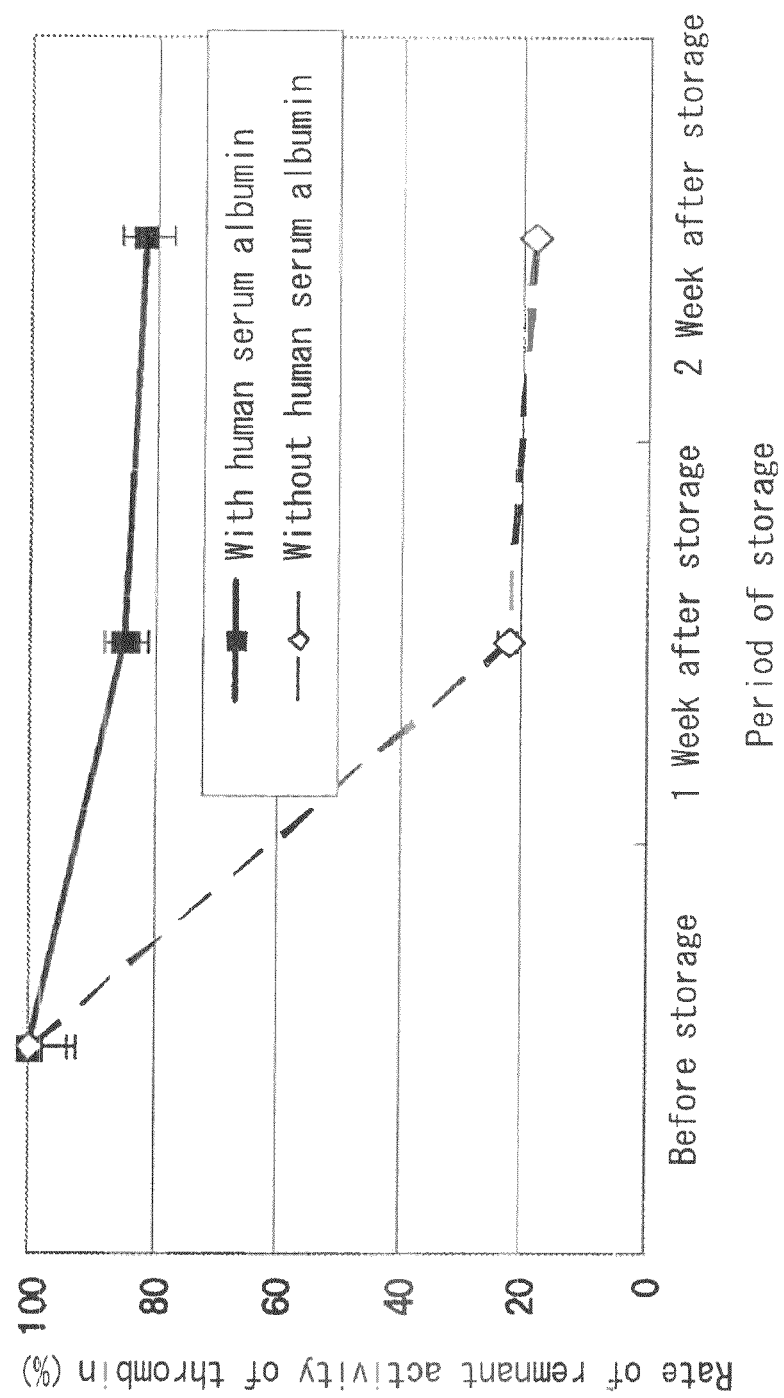
FIG. 3 shows a remnant activity of thrombin after storage for a fixed time in a bioabsorbable sheet preparation holding thrombin prepared with a thrombin solution with and without addition of human serum albumin.

One and two weeks after storage, the sample packages were opened, the thrombin eluate was obtained and the remnant activity of thrombin as maintained relative to the activity before storage was measured and indicated in graph as shown in FIG. 3.

As a result, two weeks after storage, the sample with addition of human serum albumin maintained 80% of the activity before storage but the sample without addition of human serum albumin showed the activity reduced to 20%.

Example 4

Effect of Addition of Oligosaccharide on Stability of Thrombin

Figure 4:
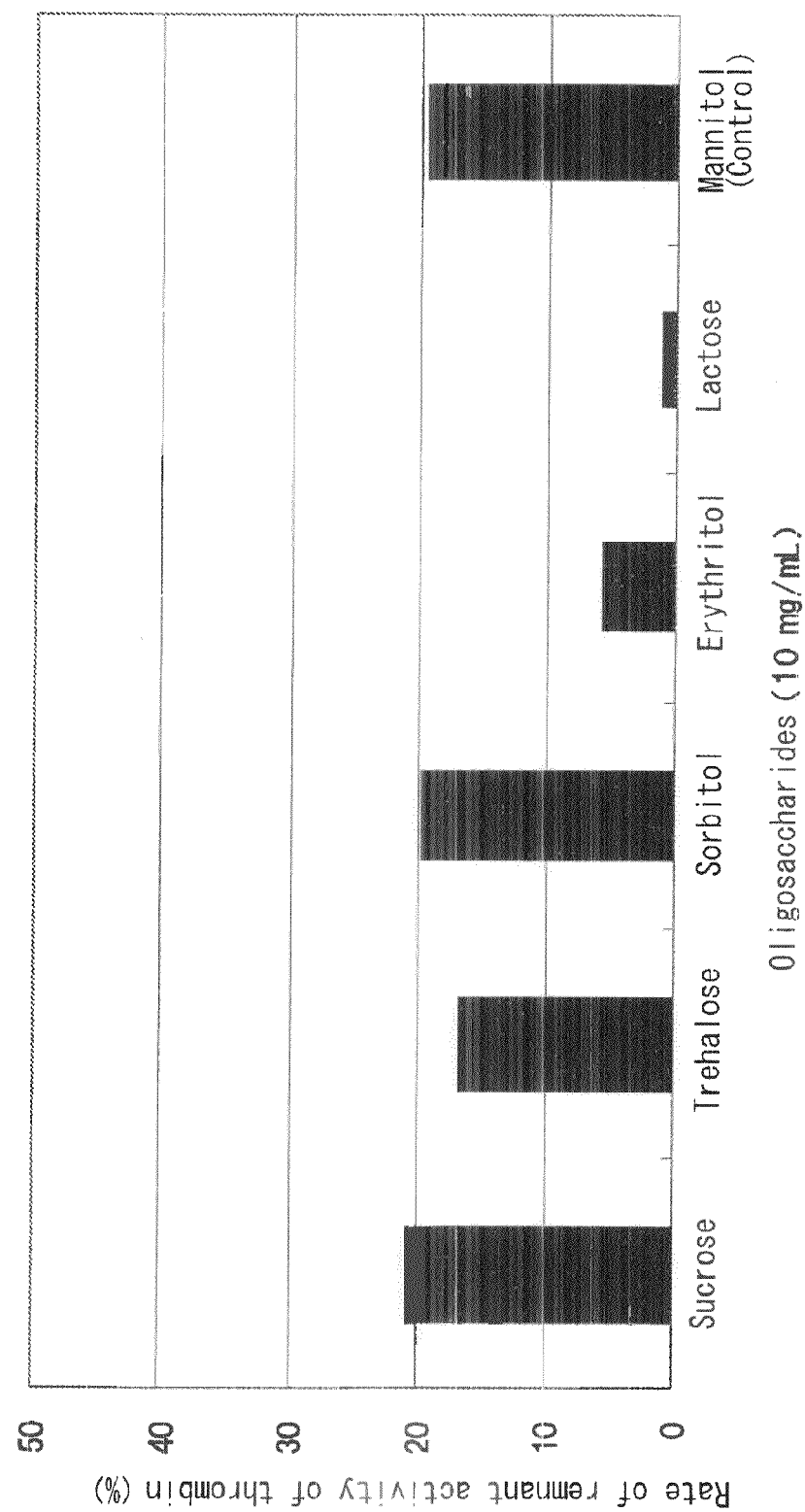
FIG. 4 shows a remnant activity of thrombin after storage for a fixed time in a bioabsorbable sheet preparation holding thrombin prepared with a thrombin solution with addition of various oligosaccharides.

Using the thrombin solution with the composition as shown in Table 1, bioabsorbable sheet preparations holding thrombin were prepared with tight sealing and packaging and stored at 65° C. as described in Examples 1 and 2. For the oligosaccharide in Table 1, sucrose, trehalose, sorbitol, erythritol, lactose, and as a control, mannitol, which is a constituent previously reported, were used. Eight days after storage, the sample packages were opened, the thrombin eluate was obtained and the remnant activity of thrombin as maintained relative to the activity before storage was measured and indicated in graph as shown in FIG. 4.

As a result, it was proved that sucrose, trehalose and sorbitol exhibited the equivalent stabilizing effect on thrombin to mannitol.

TABLE 1

|  | Thrombin solution |
| --- | --- |
| Thrombin | 1,000 Units/mL |
| Oligosaccharide | 10 mg/mL |
| Glycerol | 1% |
| Human serum albumin | 10 mg/mL |
| Tween 80 | 0.1% |
| Citrate buffer | 50 mM, pH 6.0 |

Example 5

Effect of Concentration of Oligosaccharide on Stability of Thrombin

Figure 5:
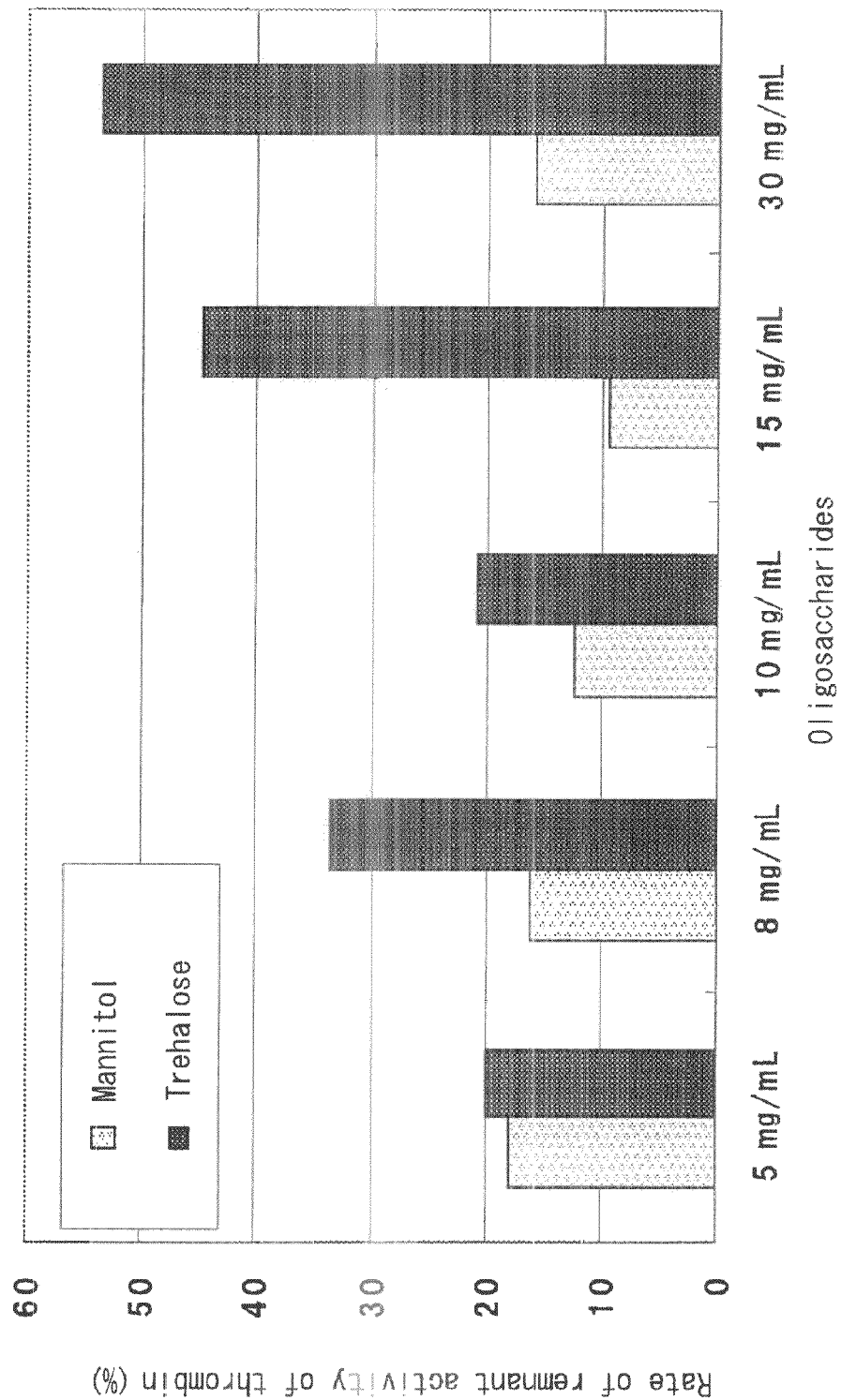
FIG. 5 shows a remnant activity of thrombin after storage for a fixed time in a bioabsorbable sheet preparation holding thrombin prepared with a thrombin solution with addition of mannitol or trehalose at various concentrations.

Using the thrombin solution with the composition as shown in Table 2 which contains an oligosaccharide at a concentration of either 5, 8, 10, 15 or 30 mg/mL, bioabsorbable sheet preparations holding thrombin were prepared with tight sealing and packaging and stored at 65° C. as described in Examples 1 and 2. Three days after storage, the sample packages were opened, the thrombin eluate was obtained and the remnant activity of thrombin was measured. For the oligosaccharide in Table 2, mannitol and trehalose were used. As shown in the graph of FIG. 5, it was proved that, at a high concentration of 8 mg/mL or more, trehalose was more excellent in the effect of maintaining the activity than mannitol.

TABLE 2

|  | Thrombin solution |
| --- | --- |
| Thrombin | 1,875 Units/mL |
| Oligosaccharide | 5, 8, 10, 15, 30 mg/mL |
| Glycerol | 1% |
| Human serum albumin | 10 mg/mL |
| Tween 80 | 0.1% |
| Citrate buffer | 50 mM, pH 6.0 |

Example 6

Effect of Addition of Amino Acid on Stability of Thrombin

Using the thrombin solution with the composition as shown in Table 3, bioabsorbable sheet preparations holding thrombin were prepared with tight sealing and packaging and stored at 65° C. as described in Examples 1 and 2. For the amino acid in Table 3, glycine as a simple amino acid, glutamic acid and aspartic acid as an acidic amino acid, arginine, histidine and lysine as a basic amino acid were used. As a control, a thrombin solution without addition of an amino acid and a thrombin solution containing human serum albumin in place of an amino acid were used.

Eight days after storage, the sample packages were opened, the thrombin eluate was obtained and the activity of thrombin was measured to obtain the remnant activity relative to the activity of the eluate before storage.

Figure 6:
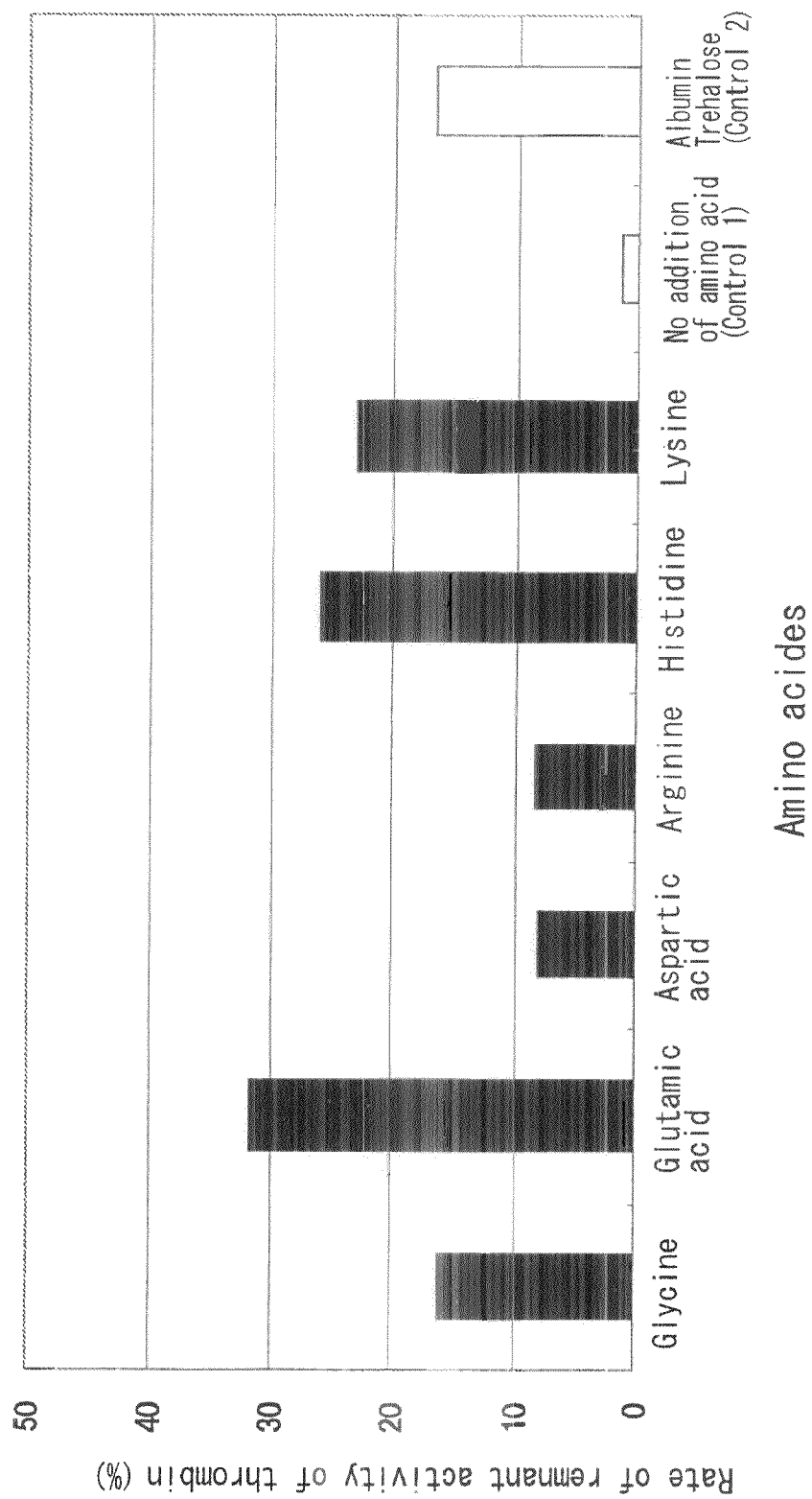
FIG. 6 shows a remnant activity of thrombin after storage for a fixed time in a bioabsorbable sheet preparation holding thrombin prepared with a thrombin solution with addition of various amino acids.

As shown in the graph of FIG. 6, it was proved that, as compared to the bioabsorbable sheet preparations holding thrombin prepared with a thrombin solution without addition of an amino acid, those prepared with a thrombin solution with addition of an amino acid were more excellent in the effect of maintaining the activity of thrombin. The groups with addition of glutamic acid, histidine or lysine exhibited a higher stabilizing effect than that of the bioabsorbable sheet preparation holding thrombin prepared with a thrombin solution with addition of human serum albumin.

TABLE 3

|  | With addition of amino acid | Control 1 (without addition of amino acid) | Control 2 (containing albumin) |
| --- | --- | --- | --- |
| Thrombin | 1,000 Units/mL | 1,000 Units/mL | 1,000 Units/mL |
| Amino acid | 100 mM | — | — |
| Oligosaccharide (Trehalose) | 30 mg/mL | 30 mg/mL | 10 mg/mL |
| Glycerol | 1% | 1% | 1% |
| Human serum albumin | — | — | 10 mg/mL |
| Calcium chloride | 20 mM | 20 mM | — |
| Tween 80 | 0.1% | 0.1% | 0.1% |
| Citrate buffer | 50 mM, pH 6.0 | 50 mM, pH 6.0 | 50 mM, pH6.0 |

Example 7

Investigation of Optimum Ratio of Histidine and Trehalose

Using the thrombin solution with the composition with addition of an amino acid as shown in Table 3 which contains histidine as an amino acid and trehalose as an oligosaccharide at the respective concentrations as shown in Table 4, bioabsorbable sheet preparations holding thrombin were prepared with tight sealing and packaging and stored at 65° C. as described in Examples 1 and 2. For the thrombin solutions with addition of histidine, a citrate buffer was not added. Eight days after storage, the sample packages were opened, the thrombin eluate was obtained and the activity of thrombin was measured to obtain the remnant activity after storage.

Figure 7:
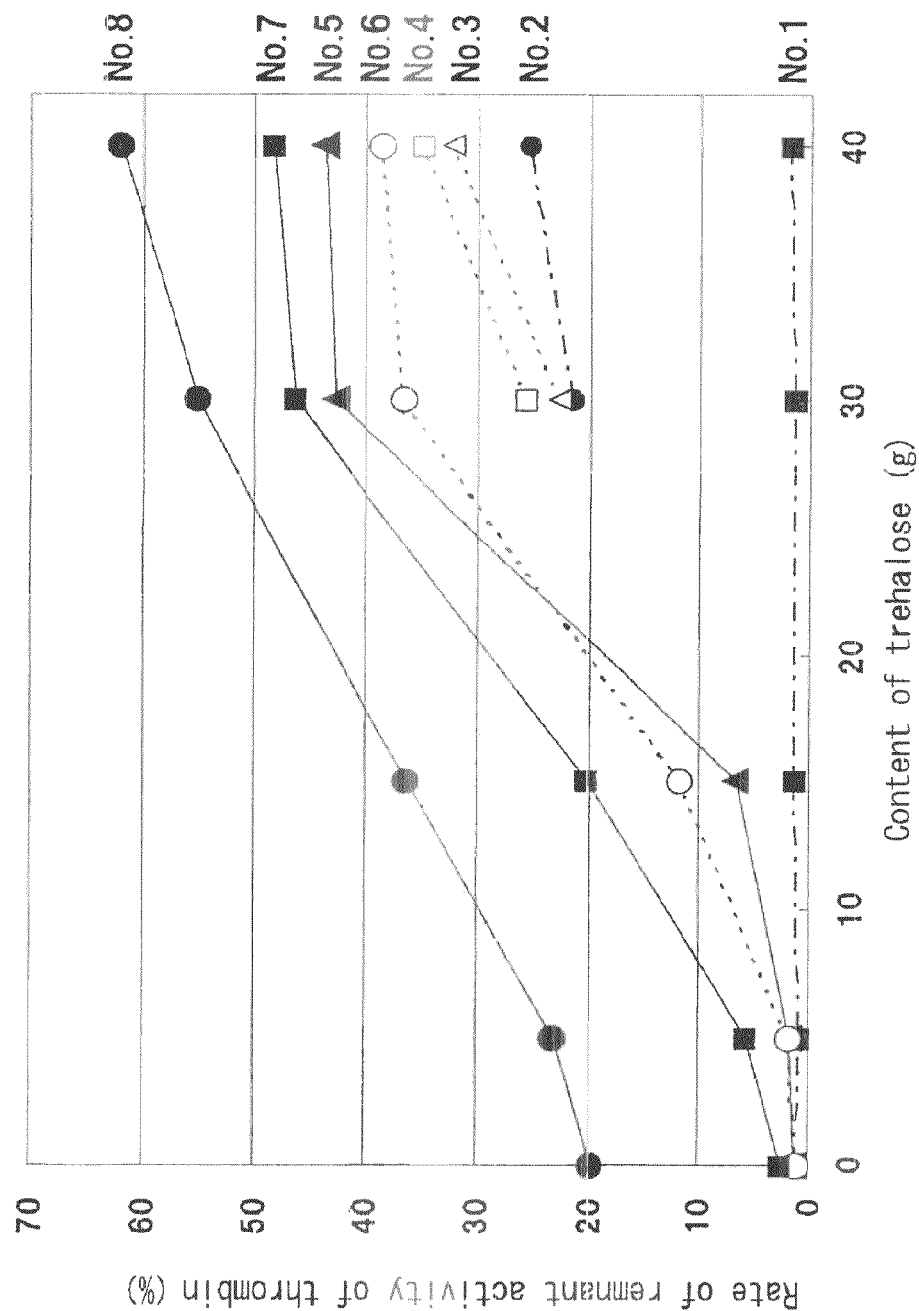
FIG. 7 shows a remnant activity of thrombin after storage for a fixed time in a bioabsorbable sheet preparation holding thrombin prepared with a thrombin solution with addition of trehalose and histidine at various concentrations. No. 1: No addition of histidine, No. 2: histidine at 2.4 mM, No. 3: histidine at 4.8 mM, No. 4: histidine at 9.6 mM, No. 5: histidine at 22.5 mM, No. 6: histidine at 45 mM, No. 7: histidine at 90 mM, No. 8: histidine at 180 mM.
Figure 8:
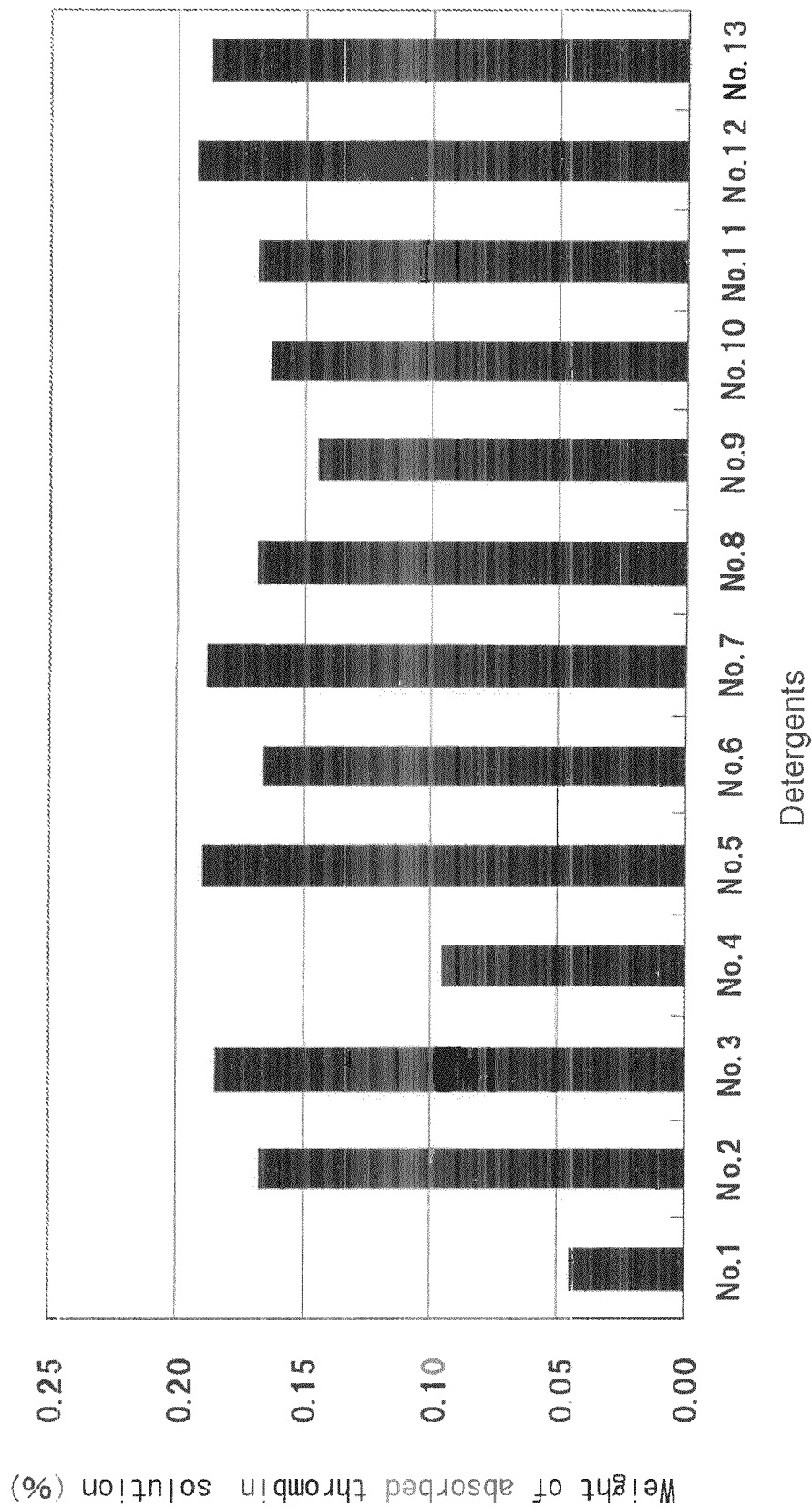
FIG. 8 shows a weight of liquid absorbed for a fixed time by a bioabsorbable sheet immersed in a thrombin solution with and without addition of various detergents. No. 1: No addition of a detergent, No. 2: Tween 80, No. 3: poly(oxyethylene) lauryl ether (Brij 35), No. 4: Pluronic F-68, No. 5: Sucrose monolaurate, No. 6: Sodium Cholate, No. 7: Tween 20, No. 8: Triton X-100, No. 9: Nonidet P40, No. 10: sulfuric-3-[(3-cholamidpropyl)-dimethylammonio]-1-propane (CHAPS), No. 11: n-Octylglucoside, No. 12: n-Dodecylmaltoside, No. 13: Digitonin.

As a result, as shown in FIG. 7, the remnant activity of thrombin was as low as 0.8 to 2.4% when trehalose at 5 to 40 mg/mL or histidine at 2.4 to 90 mM was added each alone but the remnant activity increased when trehalose and histidine were added simultaneously as compared to the addition of trehalose or histidine each alone, depending on a concentration the respective constituents.

For instance, when trehalose was at 5 mg/mL, the remnant activity increased to 5.6% to 23.1% by adding histidine at 90 to 180 mM. When trehalose was at 15 mg/mL, the remnant activity increased to 6.6% to 36.4% by adding histidine at 22.5 to 180 mM. Likewise, when trehalose was at 30 mg/mL or 40 mg/mL, the remnant activity increased to 21.4% to 62.0% by adding histidine at 2.4 to 180 mM.

The effect of addition of histidine was remarkable when trehalose was at a higher concentration. When trehalose was at 30 to 40 mg/mL, a synergetic effect could be seen even when histidine was added at a lower concentration of 2.4 mM. In particular, a synergetic effect was prominent when histidine was added at 22.5 to 180 mM where the remnant activity of thrombin increased to 35% or more.

TABLE 4

| Remnant activity of thrombin (%) | Addition of trehalose at | | | | |
|---|---|---|---|---|---|
| | 0 mg/mL | 5 mg/mL | 15 mg/mL | 30 mg/mL | 40 mg/mL |
| *   0 mM | 1.0 | 0.8 | 1.2 | 1.2 | 1.6 |
|  2.4 mM | — | — | — | 21.4 | 25.3 |
|  4.8 mM | — | — | — | 22.7 | 32.3 |
|  9.6 mM | — | — | — | 25.6 | 34.9 |
| 22.5 mM | 1.3 | 1.6 | 6.6 | 42.7 | 43.6 |
| 45 mM | 1.0 | 1.7 | 11.8 | 36.5 | 38.5 |
| 90 mM | 2.4 | 5.6 | 20.2 | 46.4 | 48.3 |
| 180 mM | 19.7 | 23.1 | 36.4 | 55.2 | 62.0 |

*: Addition of histidine at:

Example 8

Effect of Addition of Detergent on Permeation of Thrombin Solution into Sheet The bioabsorbable sheet described in Example 1 was immersed in a thrombin solution with the composition as shown in Table 5 for 15 seconds and increase in a weight of the sheet after immersion was measured. For the detergent in Table 5, Tween 80, poly(oxyethylene lauryl ether (Brij 35), Pluronic F-68, Sucrose monolaurate, Sodium Cholate, Tween 20, Triton X-100, Nonidet P40, sulfuric-3-[(3-cholamidpropyl)dimethylammonio]-1-propane (CHAPS), n-Octylglucoside, n-Dodecylmaltoside and Digitonin were used.

As shown in FIG. 6, the addition of various detergents improved permeability of the thrombin solution into the bioabsorbable sheet.

TABLE 5

| | Thrombin filler solution | Control |
|---|---|---|
| Thrombin | 1,000 Units/mL | 1,000 Units/mL |
| Amino acid (histidine) | 180 mM | 180 mM |
| Oligosaccharide (Trehalose) | 30 mg/mL | 30 mg/mL |
| Glycerol | 1% | 1% |
| Calcium chloride | 20 mM | 20 mM |
| Detergent | 0.1% | No addition |

Example 9

Investigation of Optimum Temperature of Tween 80

The bioabsorbable sheet described in Example 1 was immersed in a thrombin solution with the composition as shown in Table 5 containing as a detergent Tween 80 at various concentrations for 15 seconds and increase in a weight of the sheet after immersion was measured. Final concentrations of 0.0001, 0.001, 0.01, 0.1 and 1% of Tween 80 were used. As a control, the thrombin solution as shown in Table 5 with no addition of a detergent was used.

Figure 9:
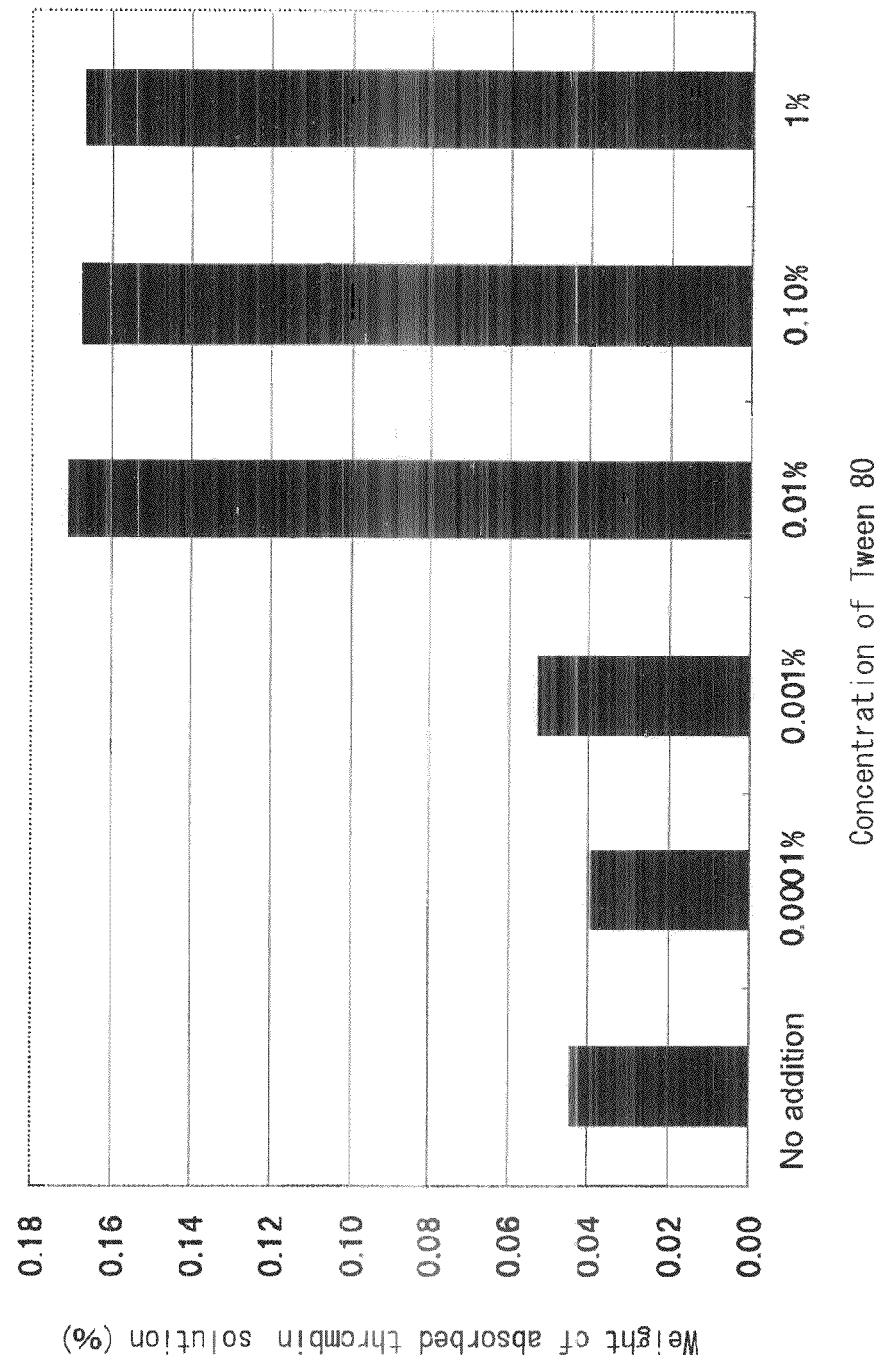
FIG. 9 shows a weight of liquid absorbed for a fixed time by a bioabsorbable sheet immersed in a thrombin solution with and without addition of Tween 80 at various concentrations.

As shown in FIG. 9, it was proved that the addition of 0.01 to 1% Tween 80 prominently improved permeability of the thrombin solution into the sheet.

Figure 10:
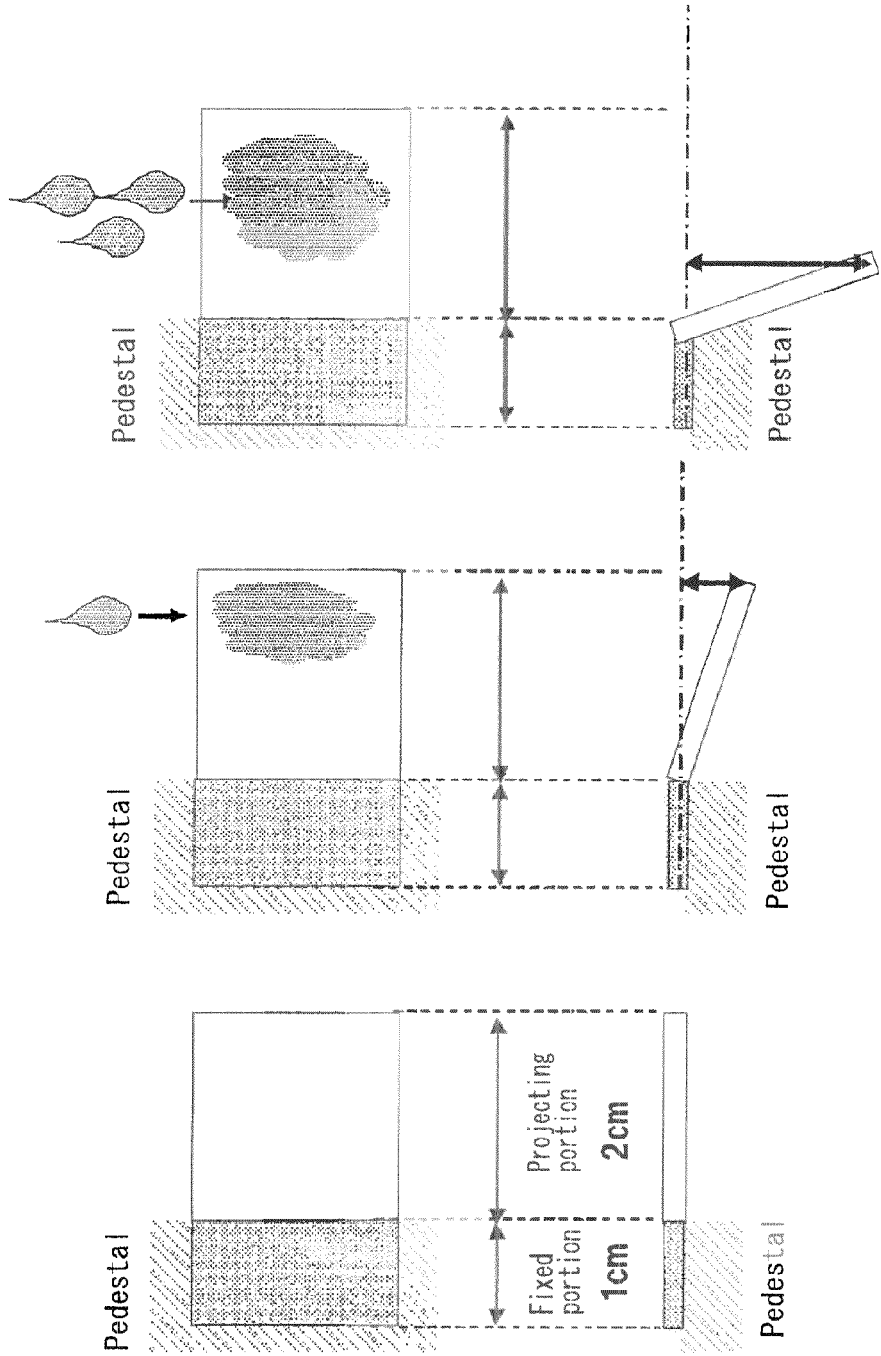
FIG. 10 shows a method of a comparative test of flexibility of a bioabsorbable sheet preparation holding thrombin.
Figure 11:
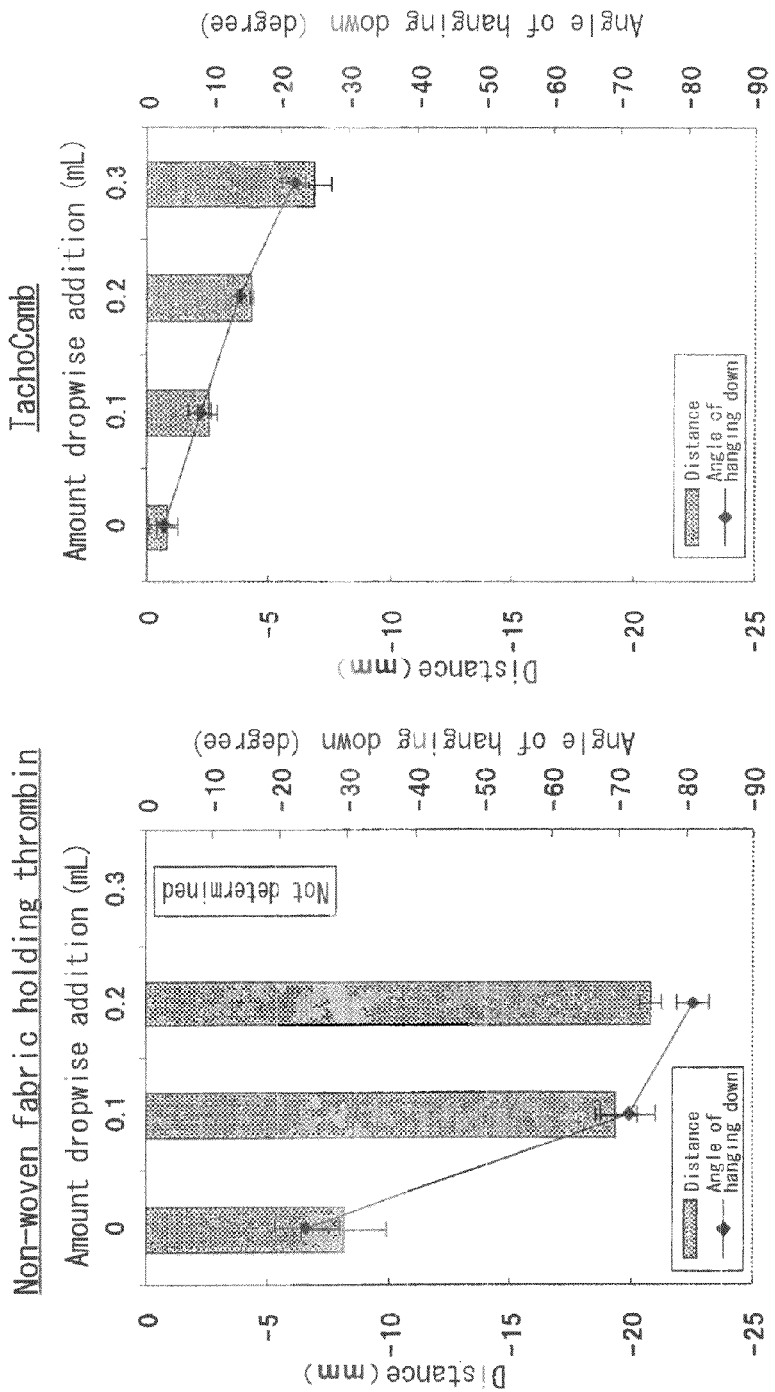
FIG. 11 shows results of a comparative test of flexibility of a bioabsorbable sheet preparation holding thrombin.

Using the thrombin solution with the composition as shown in Table 6, flexibility of the bioabsorbable sheet preparation holding thrombin prepared as described in Example 1 was estimated. As shown in FIG. 10, a portion (2 cm×1 cm) of the sheet (2 cm×3 cm) of the present invention was fixed on a pedestal and a fibrinogen solution at 55 mg/mL was added dropwise to the remaining portion (2 cm×2 cm) of the sheet horizontally projecting from the pedestal. A distance and an angle of the tip of the projecting portion as being hanged down from the horizontal level line were measured to estimate flexibility. As a control, a collagen sheet holding the constituent of a fibrin adhesive (product name: TachoComb/CSL Behling) was used. Since the control collagen sheet preparation has fibrinogen being previously held thereon by drying, a saline was used for the solution to be added dropwise and a test was performed under condition where the adhesive surface is set upside. The measurement was made after being left to stand for 5 minutes after dropwise addition of the solution and a mean value and standard deviation of three measurements were indicated in graph as shown in FIG. 11.

As a result, the control collagen sheet preparation showed a distance of hanging down of less than 5 mm at the time when 0.1 mL of the saline was added dropwise whereas the sheet of the present invention was so flexible that it has already been hanging down for its own weight before dropwise addition of the fibrinogen solution and showed a distance of hanging down of about 20 mm after dropwise addition of 0.1 mL of the fibrinogen solution. When 0.3 mL of the fibrinogen solution was added dropwise, the sheet hanged down too extensively to measure the distance.

TABLE 6

| | Thrombin filler solution |
|---|---|
| Thrombin | 1,875 Units/mL |
| Amino acid (histidine) | 180 mM |
| Oligosaccharide (trehalose) | 30 mg/mL |
| Glycerol | 1% |
| Calcium chloride | 20 mM |
| Detergent (Tween 80) | 0.1% |
| Citrate buffer | 50 mM, pH 6.0 |

INDUSTRIAL APPLICABILITY

In accordance with the present invention, a bioabsorbable sheet preparation holding thrombin and a process for preparing the same are provided. The bioabsorbable sheet preparation holding thrombin of the present invention may be prepared, for instance, by immersing a bioabsorbable sheet consisting of polyglycolic acid in a thrombin solution comprising glycerol, Tween 80, trehalose and a small amount of histidine, followed by lyophilization. By comprising glycerol, dropping off of thrombin constituent from a bioabsorbable sheet may be avoided and a bioabsorbable sheet preparation holding thrombin is endowed with flexibility. By comprising Tween 80, permeation of thrombin into a bioabsorbable sheet may be enhanced to facilitate holding of thrombin. Further, by comprising trehalose and a small amount of histidine, the activity of thrombin may sufficiently be maintained when a dry preparation is produced. Accordingly, the present invention may facilitate production of a bioabsorbable sheet preparation holding thrombin. A bioabsorbable sheet preparation holding thrombin as prepared by the process of the present invention may possess stability of thrombin and flexibility necessary for a bioabsorbable sheet preparation.

Also, with the bioabsorbable sheet preparation holding thrombin of the present invention, since thrombin may be eluted into a solution quite rapidly, thrombin may exert its enzymatic activity immediately after a sheet holding thrombin is in contact with liquid fibrinogen or blood. Namely, it is expected that, with the bioabsorbable sheet preparation holding thrombin of the present invention, thrombin may be eluted rapidly at the surface to be closed by adhesion or at active bleeding spot to exert its enzymatic activity with fibrinogen as a substrate to promptly provide fibrin conversion, providing tissue adhesion/closing effect and hemostatic effect.

The invention claimed is:

1. A bioabsorbable sheet preparation, comprising:
   1,000 to 2,000 Units/mL of thrombin,
   30 to 40 mg/mL of trehalose,
   0.01 to 1% of at least one detergent, and
   2.4 to 180 mM of histidine.
2. The preparation of claim 1, which further comprises sucrose.
3. The preparation of claim 1, which further comprises mannitol.
4. The preparation of claim 1, which further comprises sorbitol.
5. The preparation of claim 1, which further comprises erythritol.
6. The preparation of claim 1, which further comprises arginine.
7. The preparation of claim 1, further comprising lysine.
8. The preparation of claim 1, further comprising glutamic acid.
9. The preparation of claim 1, further comprising glycine.
10. The preparation of claim 1, further comprising aspartic acid.
11. The preparation of claim 1, further comprising glycerol.
12. A process for preparing the bioabsorbable sheet preparation holding thrombin of claim 1, which comprises:
    (1) preparing a solution comprising a detergent, trehalose, histidine, glycerol and thrombin;
    (2) adding dropwise the solution of (1) to a bioabsorbable sheet or immersing a bioabsorbable sheet in the solution of (1); and
    (3) drying the bioabsorbable sheet of (2).
13. The process of claim 12, wherein glycerol is at 1 to 2%.

* * * * *